US012685598B2

(12) United States Patent (10) Patent No.: US 12,685,598 B2
Maillet et al. (45) Date of Patent: Jul. 21, 2026

(54) ROBOTIC SURGERY SYSTEM WITH USER INTERFACING

(71) Applicant: ORTHOSOFT ULC, Montreal (CA)

(72) Inventors: Pierre Maillet, Mudaison (FR);
Maxence Francois, Montpellier (FR);
Jeremy Bessac, Saussan (FR)

(73) Assignee: ORTHOSOFT ULC, Montreal (CA)

( * ) Notice: Subject to any disclaimer, the term of this patent is extended or adjusted under 35 U.S.C. 154(b) by 525 days.

(21) Appl. No.: 18/308,195

(22) Filed: Apr. 27, 2023

(65) Prior Publication Data

US 2023/0346484 A1 Nov. 2, 2023

Related U.S. Application Data

(60) Provisional application No. 63/335,901, filed on Apr. 28, 2022.

(51) Int. Cl.
*A61B 34/20* (2016.01)
*A61B 34/30* (2016.01)
*A61B 90/00* (2016.01)

(52) U.S. Cl.
CPC ............. *A61B 34/20* (2016.02); *A61B 34/30* (2016.02); *A61B 2034/2055* (2016.02); *A61B 2034/2059* (2016.02); *A61B 2034/301* (2016.02); *A61B 2090/3983* (2016.02)

(58) Field of Classification Search
CPC . A61B 34/20; A61B 34/30; A61B 2034/2055;
A61B 2034/2059; A61B 2034/301; A61B
2090/3983; A61B 2034/105; A61B
2090/3762; A61B 2034/2057; A61B
2090/376
See application file for complete search history.

(56) References Cited

U.S. PATENT DOCUMENTS

| | | | |
|---|---|---|---|
| 7,668,584 B2 | 2/2010 | Jansen | |
| 9,259,278 B2 | 2/2016 | Jensen | |
| 11,397,077 B2 * | 7/2022 | Deleule | ............ G06T 7/521 |
| 2013/0211419 A1 | 8/2013 | Jensen | |
| 2018/0049809 A1 * | 2/2018 | Marti | ............ A61B 34/30 |
| 2018/0200002 A1 * | 7/2018 | Kostrzewski | ......... A61B 34/25 |
| 2018/0214221 A1 * | 8/2018 | Crawford | ............ A61B 17/00 |
| 2018/0235715 A1 * | 8/2018 | Amiot | ............ A61B 34/10 |

(Continued)

*Primary Examiner* — Sohana Tanju Khayer

(74) *Attorney, Agent, or Firm* — NORTON ROSE FULBRIGHT CANADA LLP

(57) ABSTRACT

A system for tracking an end effector of a robot in computer-assisted surgery, may have: a processing unit; and a non-transitory computer-readable memory communicatively coupled to the processing unit and comprising computer-readable program instructions executable by the processing unit for: obtaining referential tracking data for a first part of a robot using optical tracking relative to a frame of reference, and concurrently obtaining tool tracking data for an end effector of the robot arm in the frame of reference; and continuously tracking and outputting the position and orientation of the end effector in the frame of reference, using the tool tracking data, and concurrently adjusting the position and orientation of the end effector in the frame of reference when the referential tracking data indicates a movement of the first part of the robot and/of the optical tracking, in the frame of reference.

7 Claims, 7 Drawing Sheets

(56) References Cited

U.S. PATENT DOCUMENTS

| | | | |
|---|---|---|---|
| 2018/0271511 A1 | 9/2018 | Stanton | |
| 2019/0038366 A1* | 2/2019 | Johnson | A61B 90/98 |
| 2020/0281667 A1* | 9/2020 | Blondel | A61N 5/10 |
| 2021/0030479 A1* | 2/2021 | Marti | A61B 34/20 |
| 2022/0048199 A1* | 2/2022 | Heidemann | G06T 7/73 |
| 2022/0061921 A1* | 3/2022 | Crawford | G06T 7/74 |
| 2022/0110701 A1 | 4/2022 | Crawford et al. | |
| 2023/0255716 A1* | 8/2023 | Mantri | A61B 90/06 |
| | | | 600/587 |
| 2024/0050171 A1* | 2/2024 | Kostrzewski | B25J 15/0019 |
| 2025/0049517 A1* | 2/2025 | Dippel | A61B 34/30 |

* cited by examiner

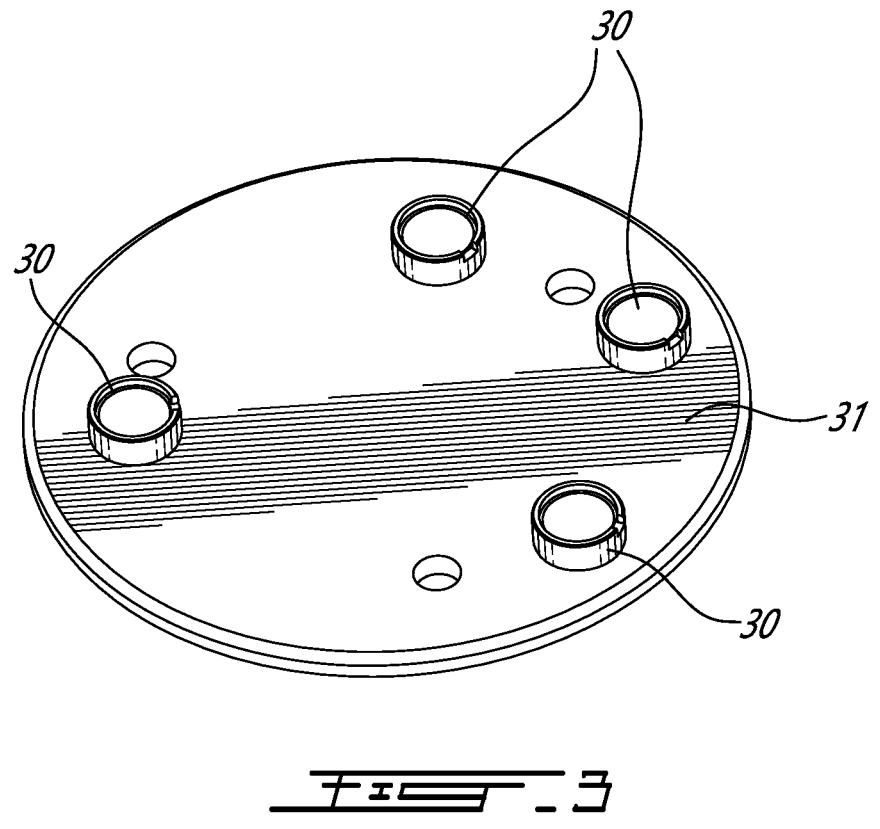
_FIG_.3
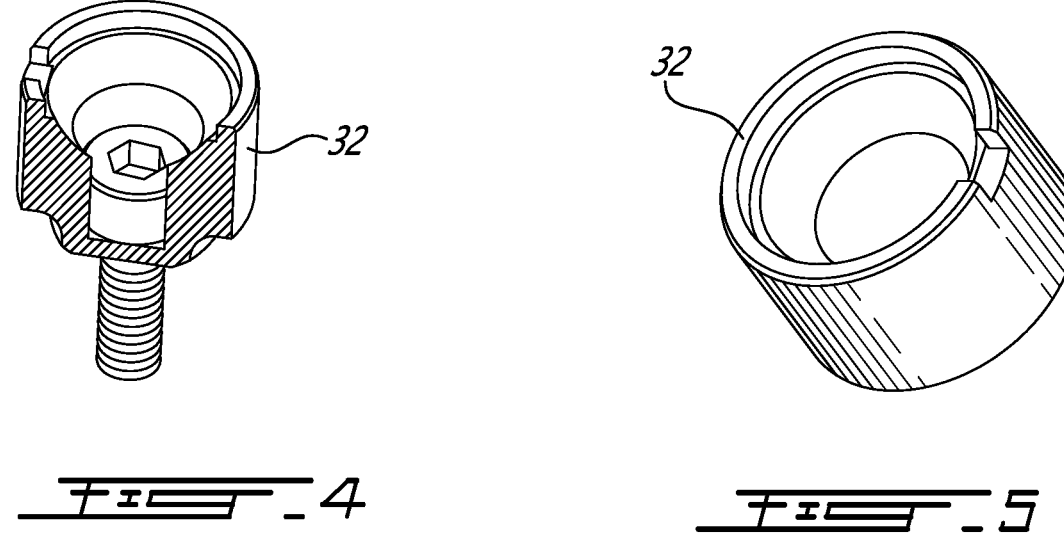
_FIG_.4
_FIG_.5

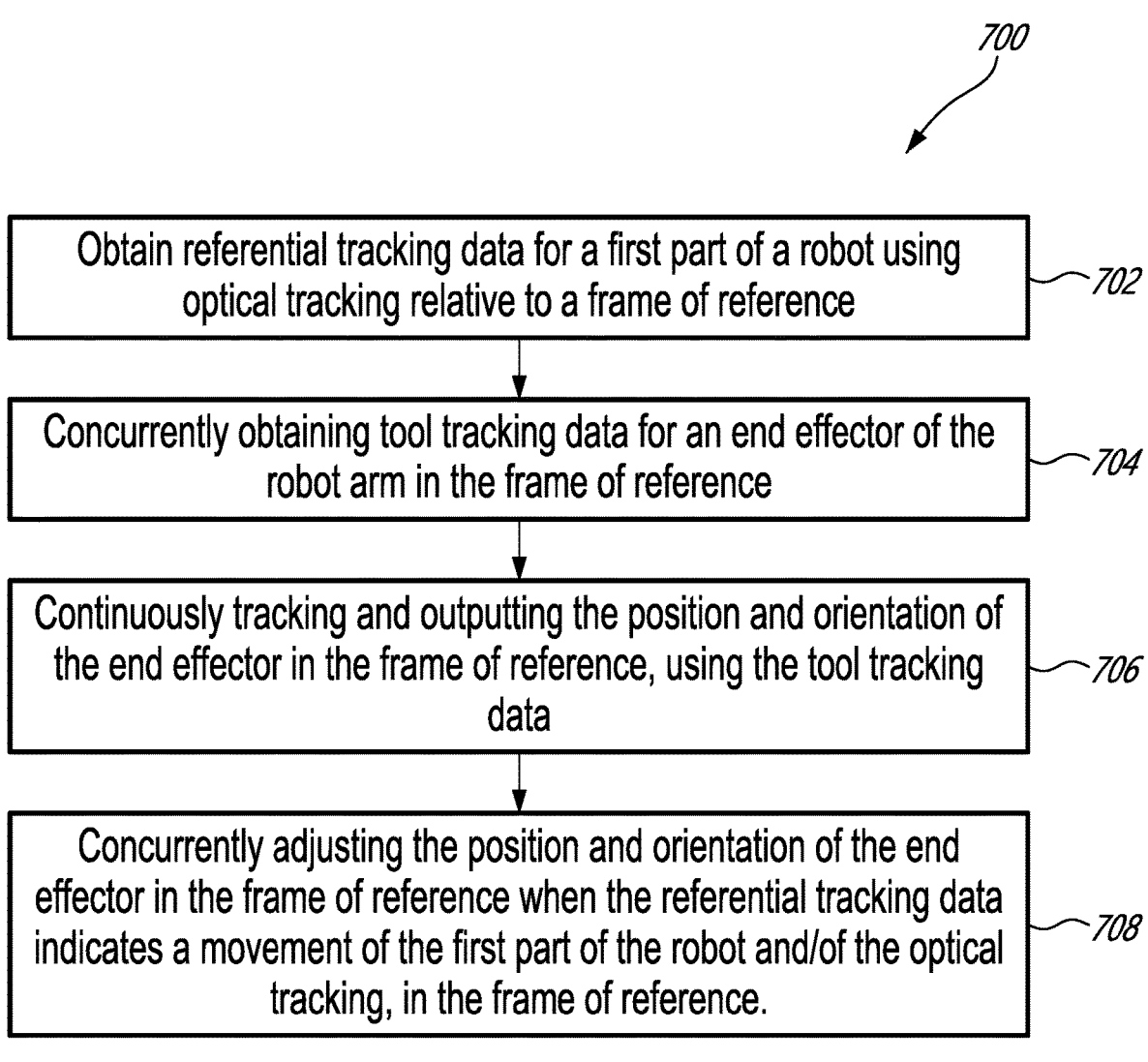

*700*

Obtain referential tracking data for a first part of a robot using optical tracking relative to a frame of reference ⟶ *702*

Concurrently obtaining tool tracking data for an end effector of the robot arm in the frame of reference ⟶ *704*

Continuously tracking and outputting the position and orientation of the end effector in the frame of reference, using the tool tracking data ⟶ *706*

Concurrently adjusting the position and orientation of the end effector in the frame of reference when the referential tracking data indicates a movement of the first part of the robot and/of the optical tracking, in the frame of reference. ⟶ *708*

FIG. 7

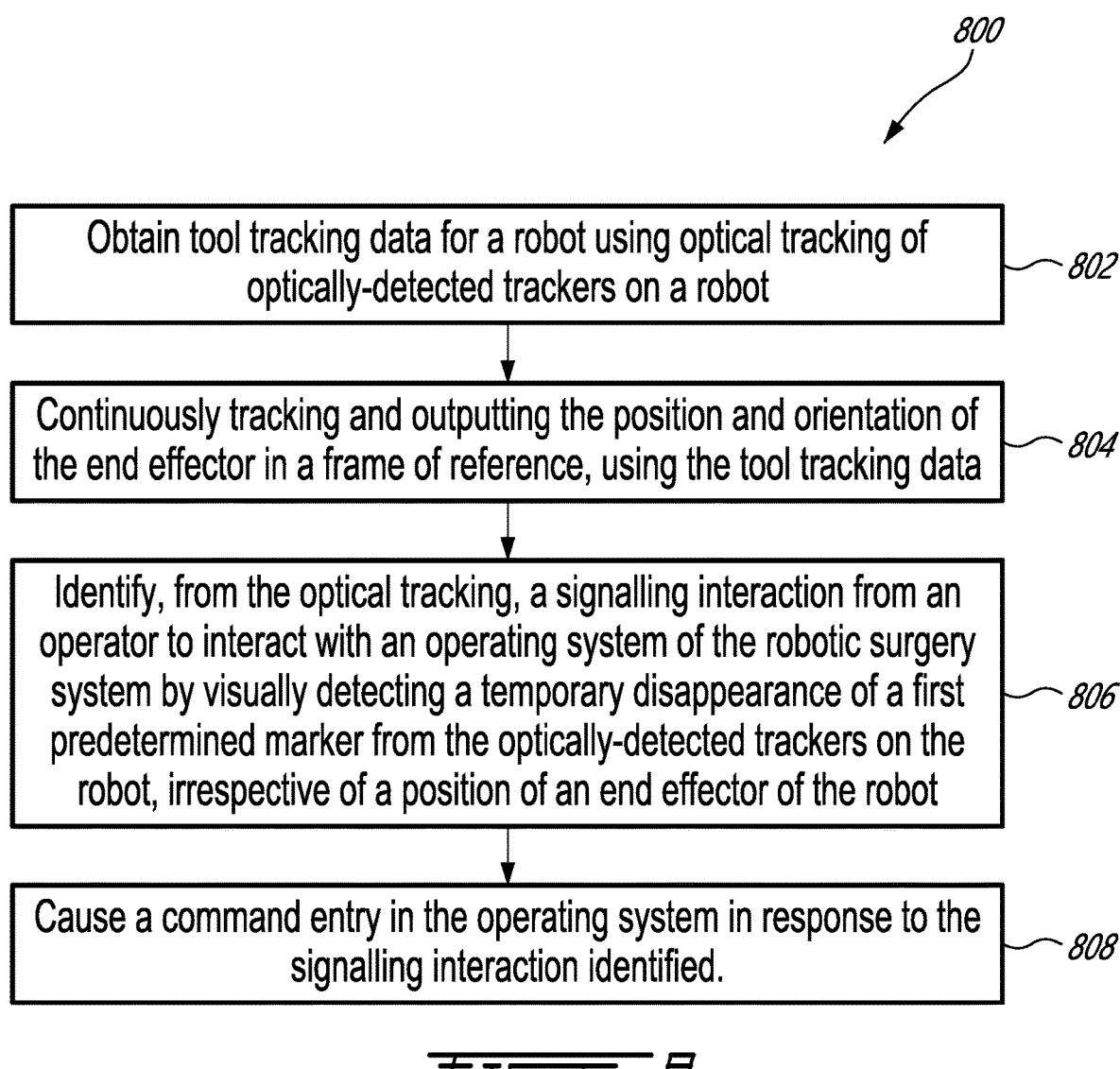

*800*

Obtain tool tracking data for a robot using optical tracking of optically-detected trackers on a robot — *802*

Continuously tracking and outputting the position and orientation of the end effector in a frame of reference, using the tool tracking data — *804*

Identify, from the optical tracking, a signalling interaction from an operator to interact with an operating system of the robotic surgery system by visually detecting a temporary disappearance of a first predetermined marker from the optically-detected trackers on the robot, irrespective of a position of an end effector of the robot — *806*

Cause a command entry in the operating system in response to the signalling interaction identified. — *808*

FIG. 8

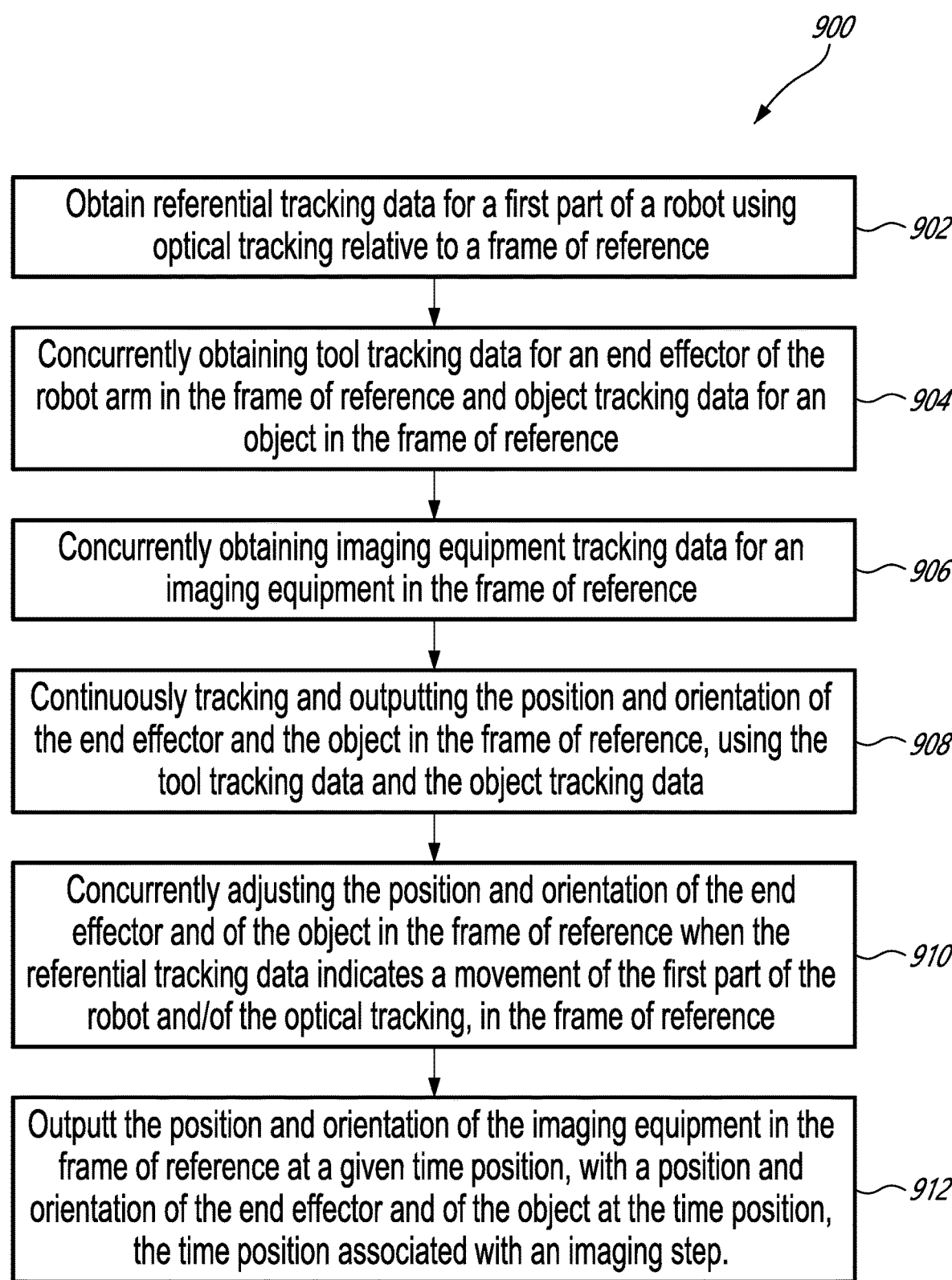

*900*

Obtain referential tracking data for a first part of a robot using optical tracking relative to a frame of reference — *902*

Concurrently obtaining tool tracking data for an end effector of the robot arm in the frame of reference and object tracking data for an object in the frame of reference — *904*

Concurrently obtaining imaging equipment tracking data for an imaging equipment in the frame of reference — *906*

Continuously tracking and outputting the position and orientation of the end effector and the object in the frame of reference, using the tool tracking data and the object tracking data — *908*

Concurrently adjusting the position and orientation of the end effector and of the object in the frame of reference when the referential tracking data indicates a movement of the first part of the robot and/of the optical tracking, in the frame of reference — *910*

Outputt the position and orientation of the imaging equipment in the frame of reference at a given time position, with a position and orientation of the end effector and of the object at the time position, the time position associated with an imaging step. — *912*

FIG. 9

ROBOTIC SURGERY SYSTEM WITH USER INTERFACING

CROSS-REFERENCE TO RELATED APPLICATION

The present application claims the priority of United States Patent Application Publication No. 63/335,901, filed on Apr. 28, 2022, the contents of which are incorporated herein by reference.

TECHNICAL FIELD

The present application relates to robotized computer-assisted surgery including bone and tool tracking, and to surgical workflows and interfacing actions associated with the surgical workflows.

BACKGROUND OF THE ART

Tracking of surgical instruments or tools is an integral part of computer-assisted surgery (hereinafter "CAS"), including robotized CAS. The end effector, the tools, bodily parts are tracked for position and/or orientation in such a way that relative navigation information pertaining to bodily parts is obtained. The information is then used in various interventions (e.g., orthopedic surgery, neurological surgery) with respect to the body, such as bone alterations, implant positioning, incisions and the like during surgery.

In robotized CAS, optical tracking is commonly used in different forms, for instance by the presence of optically-detectable trackers on the end effector and/or operating end of a robotic arm, in addition to being optionally present on the patient. For example, the optically-detectable trackers are passive retroreflective components on the robot, on tools and bones. In order to obtain values for position and/or orientation, the optical elements must be in the line of sight of the optical tracker device, and must not be obstructed. If the line of sight is disrupted, tracking may be paused, as a possible consequence. In automated robotic surgery, the interruption of optical tracking may result in the need for human intervention. Moreover, the environment of a surgical room may impose some constraints, such as the need to maintain a sterile zone and drape a robotic arm, among other issues. Also, because of space limitations and/or the volume of optical tracking equipment and robotic platform, personnel may accidentally come into contact with the robotic arm and/or optical sensor device, and this may have an impact on optical tracking calibration. There remains room for improvement.

SUMMARY

In accordance with a first aspect of the present disclosure, there is provided a system for tracking an end effector of a robot in computer-assisted surgery, comprising: a processing unit; and a non-transitory computer-readable memory communicatively coupled to the processing unit and comprising computer-readable program instructions executable by the processing unit for obtaining referential tracking data for a first part of a robot using optical tracking relative to a frame of reference, and concurrently obtaining tool tracking data for an end effector of the robot arm in the frame of reference; and continuously tracking and outputting the position and orientation of the end effector in the frame of reference, using the tool tracking data, and concurrently adjusting the position and orientation of the end effector in the frame of reference when the referential tracking data indicates a movement of the first part of the robot and/of the optical tracking, in the frame of reference.

Further in accordance with the first aspect, for instance, the computer-readable program instructions are executable by the processing unit for obtaining object tracking data for an object in the frame of reference, concurrently with obtaining the tool tracking data.

Still further in accordance with the first aspect, for instance, the computer-readable program instructions are executable by the processing unit for: continuously tracking and outputting the position and orientation of the object in the frame of reference, using the object tracking data, concurrently with tracking the end effector in the frame of reference, and concurrently adjusting the position and orientation of the object in the frame of reference when the referential tracking data indicates the movement of the first part of the robot and/of the optical tracking.

Still further in accordance with the first aspect, for instance, the computer-readable program instructions are executable by the processing unit for controlling the robot arm as a function of a position and orientation of the object.

Still further in accordance with the first aspect, for instance, the system performs the concurrently obtaining tool tracking data with sensors in the robot arm and/or with optical tracking.

Still further in accordance with the first aspect, for instance, the first part of the robot is separated from the optical tracking by a surgical drape, the system obtaining the referential tracking data for the first part of the robot by using the optical tracking through the surgical drape.

Still further in accordance with the first aspect, for instance, the first part of the robot is a base of the robot.

Still further in accordance with the first aspect, for instance, the computer-readable program instructions are executable by the processing unit for obtaining redundant readings when obtaining referential tracking data for a first part of a robot using optical tracking relative to a frame of reference.

Still further in accordance with the first aspect, for instance, the computer-readable program instructions are executable by the processing unit for obtaining imaging equipment tracking data for an imaging equipment in the frame of reference, concurrently with obtaining the tool tracking data.

Still further in accordance with the first aspect, for instance, the computer-readable program instructions are executable by the processing unit for: outputting the position and orientation of the imaging equipment in the frame of reference at a given time position, with a position and orientation of the end effector and of the object at the time position, the time position associated with an imaging step.

Still further in accordance with the first aspect, for instance, the system performs the concurrently obtaining tool tracking data with optical tracking, and wherein the computer-readable program instructions are executable by the processing unit for identifying, from the optical tracking, a signalling interaction from an operator to interact with an operating system of the robotic surgery system by visually detecting a temporary disappearance of a first predetermined tracker from the optically-detected trackers on the robot, irrespective of a position of an end effector of the robot.

Still further in accordance with the first aspect, for instance, the computer-readable program instructions are executable by the processing unit for causing a command entry in the operating system in response to the signalling interaction identified.

Still further in accordance with the first aspect, for instance, the computer-readable program instructions are executable by the processing unit for identifying, from the optical tracking, a signalling interaction from the operator to interact with the operating system of the robotic surgery system by visually detecting a temporary disappearance of a second predetermined tracker from the optically-detected trackers on the robot.

In accordance with a second aspect, there is provided a system for operating a robotic surgery system, comprising: a processing unit; and a non-transitory computer-readable memory communicatively coupled to the processing unit and comprising computer-readable program instructions executable by the processing unit for: obtaining tool tracking data for a robot using optical tracking of optically-detected trackers on a robot; continuously tracking and outputting the position and orientation of the end effector in a frame of reference, using the tool tracking data; and identifying, from the optical tracking, a signalling interaction from an operator to interact with an operating system of the robotic surgery system by visually detecting a temporary disappearance of a first predetermined tracker from the optically-detected trackers on the robot, irrespective of a position of an end effector of the robot; and causing a command entry in the operating system in response to the signalling interaction identified.

Further in accordance with the second aspect, for instance, the computer-readable program instructions are executable by the processing unit for obtaining object tracking data for an object.

Still further in accordance with the second aspect, for instance, the computer-readable program instructions are executable by the processing unit for continuously tracking and outputting the position and orientation of the object in the frame of reference, using the object tracking data, concurrently with tracking the tool in the frame of reference.

Still further in accordance with the second aspect, for instance, the computer-readable program instructions are executable by the processing unit for controlling the robot as a function of a position and orientation of the object.

Still further in accordance with the second aspect, for instance, the predetermined tracker is separated from the optical tracking by a surgical drape, the system obtaining the tool tracking data of the robot and identifying the signalling interaction by using the optical tracking through the surgical drape.

Still further in accordance with the second aspect, for instance, the computer-readable program instructions are executable by the processing unit for identifying, from the optical tracking, a signalling interaction from the operator to interact with the operating system of the robotic surgery system by visually detecting a temporary disappearance of a second predetermined tracker from the optically-detected trackers on the robot.

Still further in accordance with the second aspect, for instance, the computer-readable program instructions are executable by the processing unit for causing another command entry in the operating system in response to the signalling interaction identified from the second predetermined tracker, the command entry associated with the second predetermined tracker differing from the command entry associated with the first predetermined tracker.

DESCRIPTION OF THE DRAWINGS

FIG. 3 is a perspective view of a structure for supporting optically-detectable trackers in accordance with an aspect of the present disclosure;

FIG. 4 is a first perspective view of a mount for lens in accordance with another aspect of the present disclosure;

FIG. 5 is a second perspective view of a mount for lens as used in the structure of FIG. 4;

FIG. 7 is a flow chart of a method for tracking an end effector of a robot in computer-assisted surgery in accordance with another aspect of the present disclosure;

FIG. 8 is a flow chart of a method for operating a robotic surgery system in accordance with another aspect of the present disclosure; and FIG. 9 is a flow chart of another method for tracking an end effector of a robot in computer-assisted surgery in accordance with another aspect of the present disclosure.

DETAILED DESCRIPTION

Figure 1:
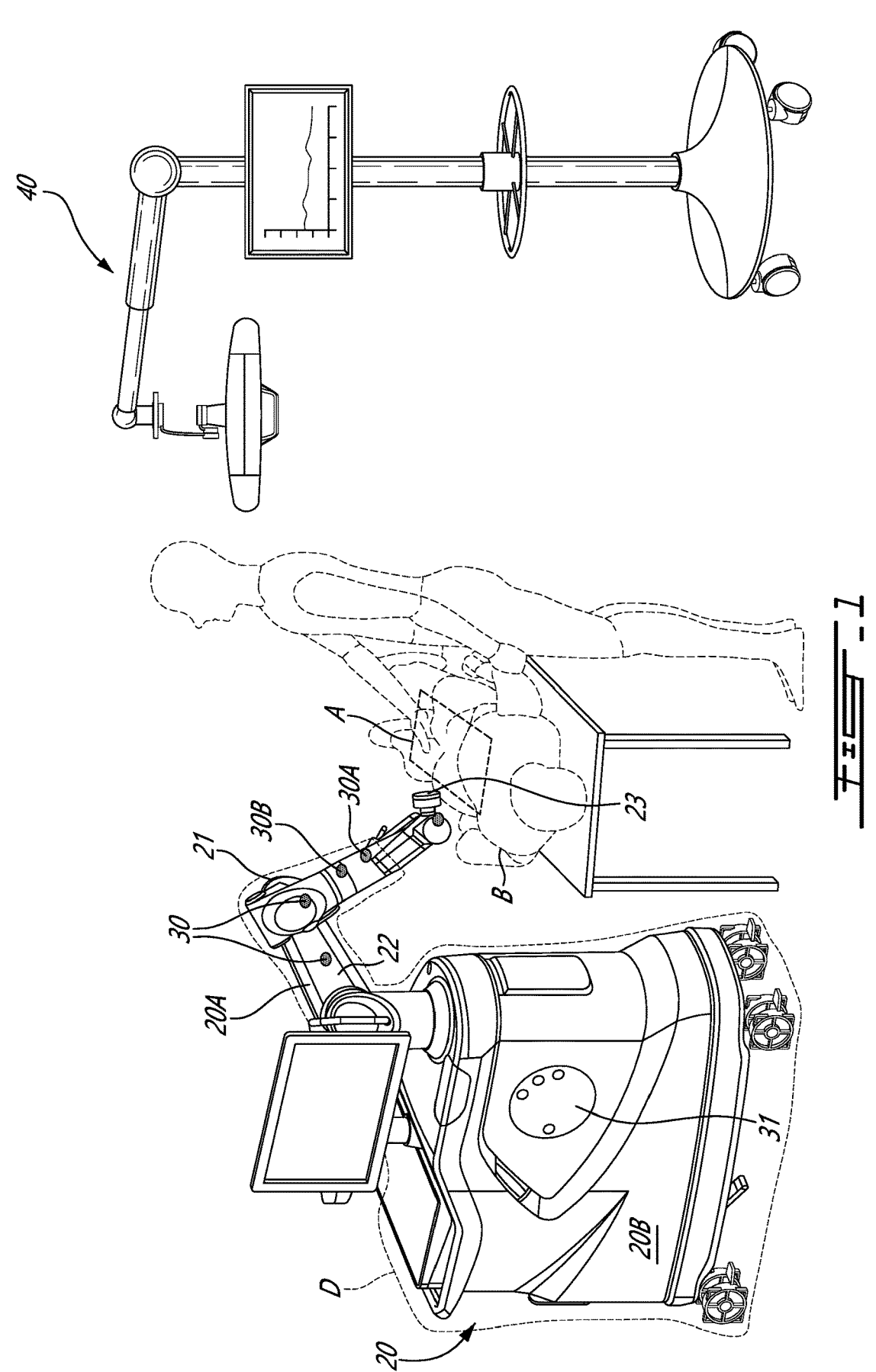
FIG. 1 is a schematic view of a robotic surgery system in accordance with an aspect of the present disclosure, relative to a patient.
Figure 2:
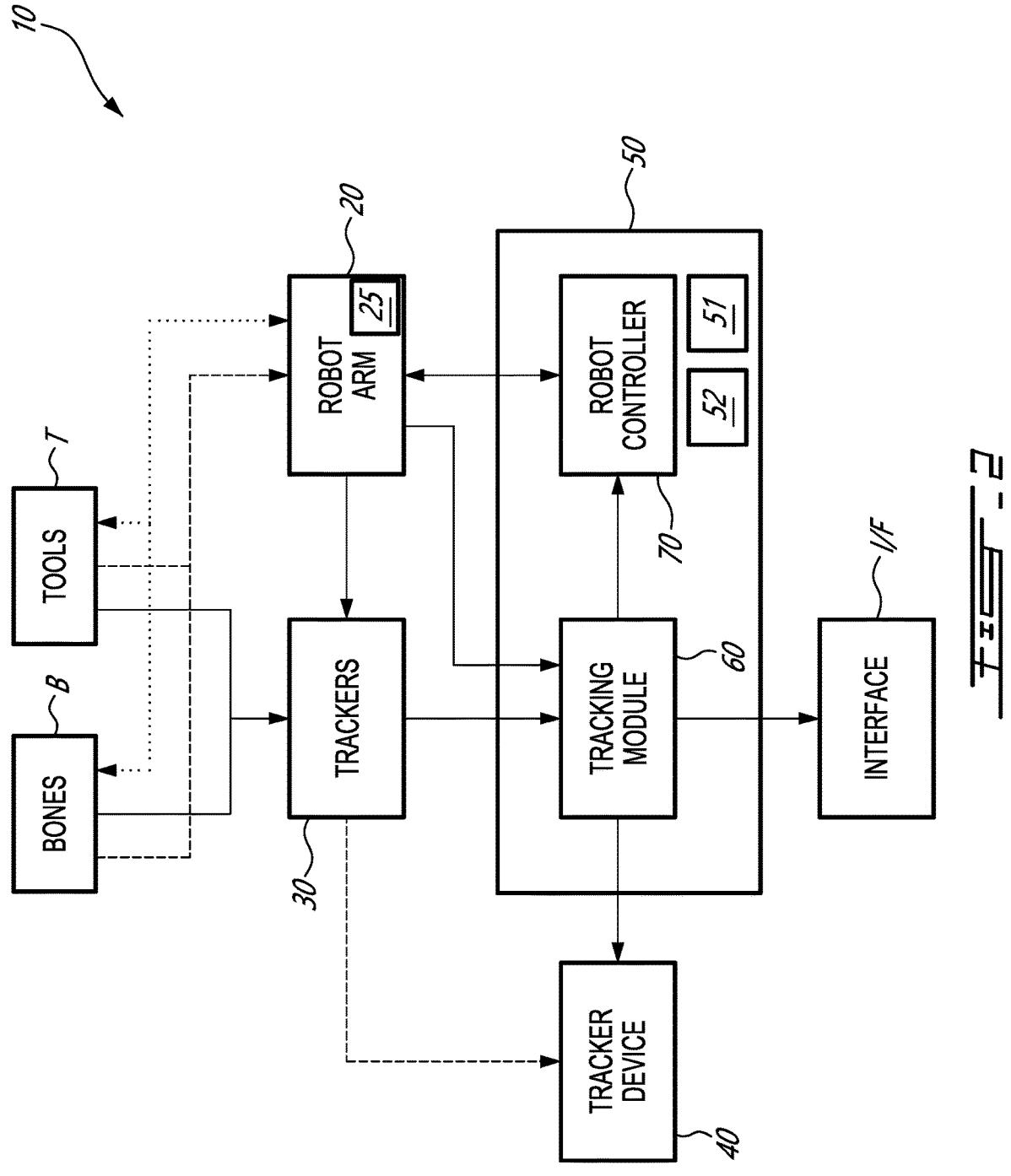
FIG. 2 is a block diagram of the tracking system for robotized computer-assisted surgery of FIG. 1.

Referring to FIGS. 1 and 2, a robotic surgery system for computer-assisted surgery (CAS) system is generally shown at 10, and is used to provide surgery assistance to an operator. For simplicity, it will be referred to herein as the system 10. In FIG. 1, the system 10 is shown relative to a dummy patient in supine decubitus, but only as an example. The system 10 could be used for any body parts, including non-exhaustively hip joint, spine, and shoulder bones, for orthopedic surgery, but could also be used in other types of surgery. For example, the system 10 could be used for surgery of all sorts, such as brain surgery, and soft tissue surgery.

The robotic surgery system 10 may be robotized in a variant, and has, may have or may be used with a robot 20, optical trackers 30, a tracker device 40, a CAS controller 50 (also known as a super controller 50), a tracking module 60, and a robot controller 70 (also known as a robot driver), or any combination thereof:

The robot 20, shown by its robot arm 20A may optionally be present as the working end of the system 10, and may be used to perform or guide bone alterations as planned by an operator and/or the CAS controller 50 and as controlled by the CAS controller 50. The robot arm 20A may also be configured for collaborative/cooperative mode in which the operator may manipulate the robot arm 20. For example, the tooling end, also known as end effector, may be manipulated by the operator while supported by the robot arm 20A. The robot 20 may be the coordinate measuring machine (CMM) of the robotic surgery system 10;

The optical trackers 30 are positioned on the robot 20, on patient tissue (e.g., bones B), and/or on the tool(s) T and surgical instruments, and provide tracking data for the robot 20, the patient and/or tools.

The tracking device 40, also known as a sensor device, apparatus, etc performs optical tracking of the optical trackers 30, so as to enable the tracking in space (a.k.a., navigation) of the robot 20, the patient and/or tools;

The CAS controller 50, also known as the super controller, includes the processor(s) and appropriate hardware and software to run a computer-assisted surgery procedure in accordance with one or more workflows. The CAS controller 50 may include or operate the tracking device 40, the tracking module 60, and/or the robot controller 70. As described hereinafter, the CAS controller 50 may also drive the robot arm 20A through a planned surgical procedure;

The tracking module 60 is tasked with determining the position and/or orientation of the various relevant objects during the surgery procedure, such as the end effector of the robot arm 20, bone(s) B and tool(s) T, using data acquired by the tracking device 40 and by the robot 20, and/or obtained from the robot controller 70. The position and/or orientation may be used by the CAS controller 50 to control the robot arm 20A;

The robot controller 70 is tasked with powering or controlling the various joints of the robot arm 20A, based on operator demands or on surgery planning. The robot controller 70 may also optionally calculate robot movements of the robot arm 20A, so as to control movements of the robot arm 20A autonomously in some instances, i.e., without intervention from the CAS controller 50;

An additional camera(s) may be present, for instance as a complementary registration tool. The camera may for instance be mounted on the robot 20A, such as on the robot arm, such that the point of view of the camera is known in the frame of reference, also known as the coordinate system.

Other components, devices, systems, may be present, such as surgical instruments and tools T, interfaces I/F such as displays, screens, computer station, servers, and like etc. Secondary tracking systems may also be used for redundancy.

Referring to FIG. 1, the robot 20 may have the robot arm 20A stand from a base 20B, for instance in a fixed relation relative to the operating-room (OR) table supporting the patient, whether it is attached or detached from the table. The robot arm 20A has a plurality of joints 21 and links 22, of any appropriate form, to support an end effector 23 that may interface with the patient, or may be used during surgery without interfacing with the patient. For example, the end effector or tool head may optionally incorporate a force/torque sensor for collaborative/cooperative control mode, in which an operator manipulates the robot arm 20A. The robot arm 20A is shown being a serial mechanism, arranged for the tool head 23 to be displaceable in a desired number of degrees of freedom (DOF). The tool head 23 may for example be a support that is not actuated, the support being used to support a tool, with the robot arm 20A used to position the tool relative to the patient. For example, the robot arm 20A controls 6-DOF movements of the tool head, i.e., X, Y, Z in the coordinate system, and pitch, roll and yaw. Fewer or additional DOFs may be present. For simplicity, only a fragmented illustration of the joints 21 and links 22 is provided, but more joints 21 of different types may be present to move the end effector 23 in the manner described above. The joints 21 are powered for the robot arm 20A to move as controlled by the CAS controller 50 in the six DOFs, and in such a way that the position and orientation of the end effector 23 in the coordinate system may be known, for instance by readings from encoders on the various joints 21. Therefore, the powering of the joints is such that the end effector 23 of the robot arm 20A may execute precise movements, such as moving along a single direction in one translation DOF, or being restricted to moving along a plane, among possibilities. Such robot arms 20A are known, for instance as described in U.S. patent application Ser. No. 11/610,728, and incorporated herein by reference.

The end effector 23 of robot arm 20A may be defined by a chuck or like tool interface, typically actuatable in rotation. As a non-exhaustive example, numerous tools may be used as end effector for the robot arm 20, such tools including a registration pointer, a reamer (e.g., cylindrical, tapered), a reciprocating saw, a retractor, a camera, an ultrasound unit, a laser rangefinder or light-emitting device (e.g., the indicator device of U.S. Pat. No. 8,882,777), a laminar spreader, an instrument holder, or a cutting guide, depending on the nature of the surgery. The various tools may be part of a multi-mandible configuration or may be interchangeable, whether with human assistance, or as an automated process. The installation of a tool in the tool head may then require some calibration in order to track the installed tool in the X, Y, Z coordinate system of the robot arm 20.

The end effector 23 of the robot arm 20A may be positioned by the robot 20 relative to surgical area A in a desired orientation according to a surgical plan, such as a plan based on preoperative imaging. Due to the proximity between the robot 20 and the surgical area A, the robot 20 may be covered partially with a surgical drape D, also known as a surgical robotic drape. The surgical drape D is a sterile panel (or panels), tubes, bags or the like that form(s) a physical barrier between the sterile zone (e.g., surgical area) and some equipment that may not fully comply with sterilization standards, such as the robot 20. In an embodiment, the surgical drape D is transparent such that one can see through the drape D. In an embodiment, the robot is entirely covered with the surgical drape D, and this includes the base 20B, but with the exception of the end effector 23. Indeed, as the end effector 23 interacts or may interact with the human body, it may be sterilized and may not need to be covered by the surgical drape D, to access the patient. Some part of the robot 20 may also be on the sterile side of the surgical drape D. In a variant, a portion of the robot arm 20 is covered by the surgical drape D. For example, the surgical drape D may be in accordance with U.S. patent application Ser. No. 15/803,247, filed on Nov. 3, 2017 and incorporated herein by reference.

In order to position the end effector 23 of the robot arm 20A relative to the patient B, the CAS controller 50 can manipulate the robot arm 20A automatically (without human intervention), or by a surgeon manually operating the robot arm 20A (e.g. physically manipulating, via a remote controller through the interface I/F) to move the end effector 23 of the robot arm 20A to the desired location, e.g., a location called for by a surgical plan to align an instrument relative to the anatomy. Once aligned, a step of a surgical procedure can be performed, such as by using the end effector 23.

As shown in FIG. 2, the robot arm 20A may include sensors 25 in its various joints 21 and links 22. The sensors 25 may be of any appropriate type, such as rotary encoders, optical sensors, position switches that are a non-exhaustive list of potential sensors, for the position and orientation of the end effector, and of the tool in the end effector 23 to be known. More particularly, the tracking module 60 may determine the position and orientation of the robot 20 in a frame of reference of the robot 20, such as by obtaining the position (x,y,z) and orientation (phi, theta, ro) of the end effector 23 from the CAS controller 50 using the sensors 25 in the robot arm 20A, i.e., robot coordinates may be an integrated function of the robot 20 in that it may determine the position and orientation of its end effector 23 with respect to its coordinate system. Using the data from the sensors 25, the robot 20 may be the coordinate measuring machine (CMM) of the robotic surgery system 10, with a frame of reference (e.g., coordinate system, referential system) of the procedure being relative to the fixed position of the base 20B of the robot 20. The sensors 25 must provide the precision and accuracy appropriate for surgical procedures. The coupling of tools to the robot arm 20A may automatically cause a registration of the position and orientation of the tools in the frame of reference of the robot 20, though steps of calibration could be performed.

Referring to FIG. 1, the trackers 30 are shown secured to the bones B and at various locations on the robot 20, and may also or alternatively be on instruments. The trackers 30 may be known as trackable elements, markers, navigation markers, active sensors (e.g., wired or wireless) that may for example include infrared emitters. In a variant, the trackers 30 are passive retro-reflective elements, that reflect light. The trackers 30 have a known geometry so as to be recognizably through detection by the tracker device 40. For example, the trackers 30 may be retro-reflective lenses. Such trackers 30 may be hemispherical in shape, by way of a shield. The shield may be hollow and may cover a reflective membrane or surface. For example, the trackers 30 may be of the type known as Radix™ lenses, from Northern Digital Inc. For example, each tracker 30 may be defined as having a shape that is substantially defined by two spherical caps (e.g., truncated spherical caps) of different radii that are disposed substantially concentric in relation to one another. The trackers 30 may further include one or more flanges and/or a uniform refractive index. A feature of such trackers 30, and of other types of trackers, resides in the fact that the trackers 30 can reflect light from the tracker device 40 in spite of the separation by the surgical drape D. Stated differently, the tracker device 40 may be on one side of the surgical drape D, while some of the trackers 30 may be on the other side of the surgical drape D, yet the tracker device 40 may still "see" (i.e., optically detect) the trackers 30. Other trackers may be used, such as those described in U.S. Pat. No. 8,386,022. In an embodiment, the trackers 30 may be active emitters.

Referring to FIG. 3, a plurality of the trackers 30 (a support therefor being support) may be held in a fixed and known geometry pattern, such as by being secured to a structure 31, in the form of a plate. The structure 31 is well suited to be used as a joint plate in the robot arm 20A, i.e., at a rotary joint between the links in the robot arm 20A. Other configurations possible, including a frame. The trackers 30 are arranged at least in a scalene triangle, if only three trackers 30 are present. FIGS. 4 and 5 show a mount 32, suitable for receiving the lens portion of the tracker 30, that may be used as an alternative to the structure 31. The mounts 32 may be fixed to the robot 20 at discrete locations, as an alternative to a structure 31 with multiple trackers 30. The structure 31, with its pattern of trackers 30, may form part of the CMM function of the robotic surgery system 10. In a variant, it is attached to a fixed part of the robotic surgery system 10, such as the base 20B of the robot arm 20. During surgery, the base 20B is not frequently moved, if moved at all, though it may be accidentally displaced. However, as set out below, the robotic surgery system 10 may use its other tracking components to account for movement, and not disrupt the surgical workflow.

As observed from FIG. 1, the robot 20 may have multiple trackers 30, in a redundant manner. In theory, a single set of three trackers 30 in a fixed relation relative to the end effector 23 may suffice for the tracking of the end effector 23. However, as observed, the robot 20 may have multiple trackers 30, to allow redundant tracking data to be available to the CAS controller 50, and hence provide the robotic surgery system 10 with more landmarks to locate itself within the frame of reference.

In FIG. 2, the tracker device 40 is shown as being embodied by an image capture device, capable of illuminating its environment. In a variant, the tracker device 40 may have two (or more) points of view, such that triangulation can be used to determine the position of the tracker devices 30 in space, i.e., the coordinate system of the robotic surgery system 10. The tracker device 40 may emit light, or use ambient light, to observe the trackers 30 from its points of view, so as to determine a position of the trackers 30 relative to itself. By knowing the geometry of the arrangements of trackers 30, such as for example that of the structure 31, the tracker device 40 can produce data enabling the locating of the structure 31, or object supporting the structure 31 and trackers 30, within the coordinate system of the robotic surgery system 10. In an embodiment, the tracker device 40 is of the type known as the Polaris products by Northern Digital Inc. The tracker device 40 may form the complementary part of the CMM function of the robotic surgery system 10, with the trackers 30 on the robot base 20A for example. In FIG. 2, the trackers 30 may be affixed with letters, such as 30A, 30B, etc, to explain some contemplated uses in relation to a surgical workflow and an operating system of the present disclosure.

Referring to FIG. 2, the CAS controller 50 is shown in greater detail relative to the other components of the robotic surgery system 10. The CAS controller 50 has a processor unit 51 and a non-transitory computer-readable memory 52 communicatively coupled to the processing unit 51 and configured for executing computer-readable program instructions executable by the processing unit 51 to perform some functions, such as tracking the patient tissue and tools, using the position and orientation data from the robot 20 and the readings from the tracker device 40. Accordingly, as part of the operation of the CAS controller 50, the computer-readable program instructions may include an operating system that may be viewed by a user or operator as a GUI on one or more of the interfaces of the robotic surgery system 10. It is via this or these interfaces that the user or operator may interface with the robotic surgery system, be guided by a surgical workflow, obtain navigation data, etc. The CAS controller 50 may also control the movement of the robot arm 20A via the robot controller module 70. The robotic surgery system 10 may comprise various types of interfaces I/F, for the information to be provided to the operator. The interfaces I/F may include and/or screens including wireless portable devices (e.g., phones, tablets), audio guidance, LED displays, head-mounted display for virtual reality, augmented reality, mixed reality, among many other possibilities. For example, the interface I/F comprises a graphic-user interface (GUI) operated by the system 10. The CAS controller 50 may also display images captured pre-operatively, or using cameras associated with the procedure (e.g., 3D camera, laparoscopic cameras, tool mounted cameras), for instance to be used in the collaborative/cooperative control mode of the system 10, or for visual supervision by the operator of the system 10, with augmented reality for example. The CAS controller 50 may drive the robot arm 20A, in performing the surgical procedure based on the surgery planning achieved pre-operatively, or in maintaining a given position and orientation to support a tool. The CAS controller 50 may run various modules, in the form of algorithms, code, non-transient executable instructions, etc, in order to operate the robotic surgery system 10 in the manner described herein. The CAS controller 50 may be part of any suitable processor unit, such as a personal computer or computers including laptops and desktops, tablets, server, etc.

The tracking module 60 may be a subpart of the CAS controller 50, or an independent module or system. The tracking module 60 receives the position and orientation data from the robot 20 and the readings from the tracker device 40. The tracking module 60 may hence determine the relative position of the objects relative to the robot arm 20A in a manner described below. The tracking module 60 may also be provided with models of the objects to be tracked. For example, the tracking module 60 may track bones and tools, and hence may use virtual bone models and tool models. The bone models may be acquired from pre-operative imaging (e.g., MRI, CT-scans), for example in 3D or in multiple 2D views, including with 2D X-ray to 3D bone model technologies. The virtual bone models may also include some image processing done preoperatively, for example to remove soft tissue or refine the surfaces that will be exposed and tracked. The virtual bone models may be of greater resolution at the parts of the bone that will be tracked during surgery, such as the knee articulation in knee surgery. The bone models may also carry additional orientation data, such as various axes (e.g., longitudinal axis, mechanical axis, etc). The bone models may therefore be patient specific. It is also considered to obtain bone models from a bone model library, with the data obtained from the video images used to match a generated 3D surface of the bone with a bone from the bone atlas. The virtual tool models may be provided by the tool manufacturer, or may also be generated in any appropriate way so as to be a virtual 3D representation of the tool(s).

Additional data may also be available, such as tool orientation (e.g., axis data and geometry). By having access to bone and tool models, the tracking module 60 may obtain additional information, such as the axes related to bones or tools.

Still referring to FIG. 2, the CAS controller 50 may have the robot controller 70 integrated therein. However, the robot controller 70 may be physically separated from the CAS controller 50, for instance by being integrated into the robot 20 (e.g., in the robot base 20B). The robot controller 70 is tasked with powering and/or controlling the various joints of the robot arm 20A. The robot controller 70 may also optionally calculate robot movements of the robot arm 20A, so as to control movements of the robot arm 20A autonomously in some instances, i.e., without intervention from the CAS controller 50. There may be some force feedback provided by the robot arm 20A to avoid damaging the bones, to avoid impacting other parts of the patient or equipment and/or personnel. The robot controller 70 may perform actions based on a surgery planning. The surgery planning may be a module programmed specifically for any given patient, according to the parameters of surgery desired by an operator such as an engineer and/or surgeon. The parameters may include geometry of selected, planned bone cuts, planned cut depths, sequence or workflow of alterations with a sequence of surgical steps and tools, tools used, etc.

As observed herein, the trackers 30 and the tracker device 40 may be complementary tracking technology. The position and orientation of the surgical tool calculated by the tracking module 60 using optical tracking may be redundant over the tracking data provided by the robot controller 70 and/or the CAS controller 50 and its embedded robot arm sensors 25. However, the redundancy may assist in ensuring the accuracy of the tracking of the surgical tool, and end effector 23. For example, the redundancy is used as a safeguard against incorrect tracking from the CAS controller 50, for instance due to relative movement between the robot 20, the tracker device 40, and the patient and/or table. Also, the tracking of the tool using the tracking module 60 may be used to detect any discrepancy between a calculated position and orientation of the surgical tool T through the sensors on the robot arm 20A and inertial sensor unit(s) 30, and the actual position and orientation of the surgical tool. For example, an improper mount of the tool T into the chuck of the robot arm 20A could be detected from the output of the tracking module 60, when verified by comparing the position and orientation from the CAS controller 50 (e.g., obtained from the encoders on the robot arm 20A) with the optical tracking on the end effector 23. The operator may be prompted to verify the mount, via the interface I/F or head-mounted display 20. Moreover, the redundancy may enable the use of some of the trackers 30 as user interfaces, for the user to communicate with the CAS controller 50.

Consequently, the tracking module 60 may combine the optical tracking data from the tracker device 40 to the position and orientation data from the sensors 25 embedded in the robot arm 20A, for the positional tracking data for the objects may be calculated by the tracking module 60, as detailed below. Therefore, the combination by the tracking module 60 of the tracking from the robot arm 20A and that from the tracker device 40 enable the tracking module 60 to track objects with a continuous and robust navigation data.

In an embodiment, the tracking module 60 uses a tracker 30 on the bone B or other body portion or OR table to obtain the orientation of the bone B in the coordinate system, and locates the bone B using other methods, such as obtaining the position and orientation of a probing tool using the encoders in the robot arm 20A, in a registration procedure described below. Stated differently, the bone B may be fixed on the OR table and the system 10 may rely on trackers 30 fixed to the OR table to optically track the bone B.

Figure 6:
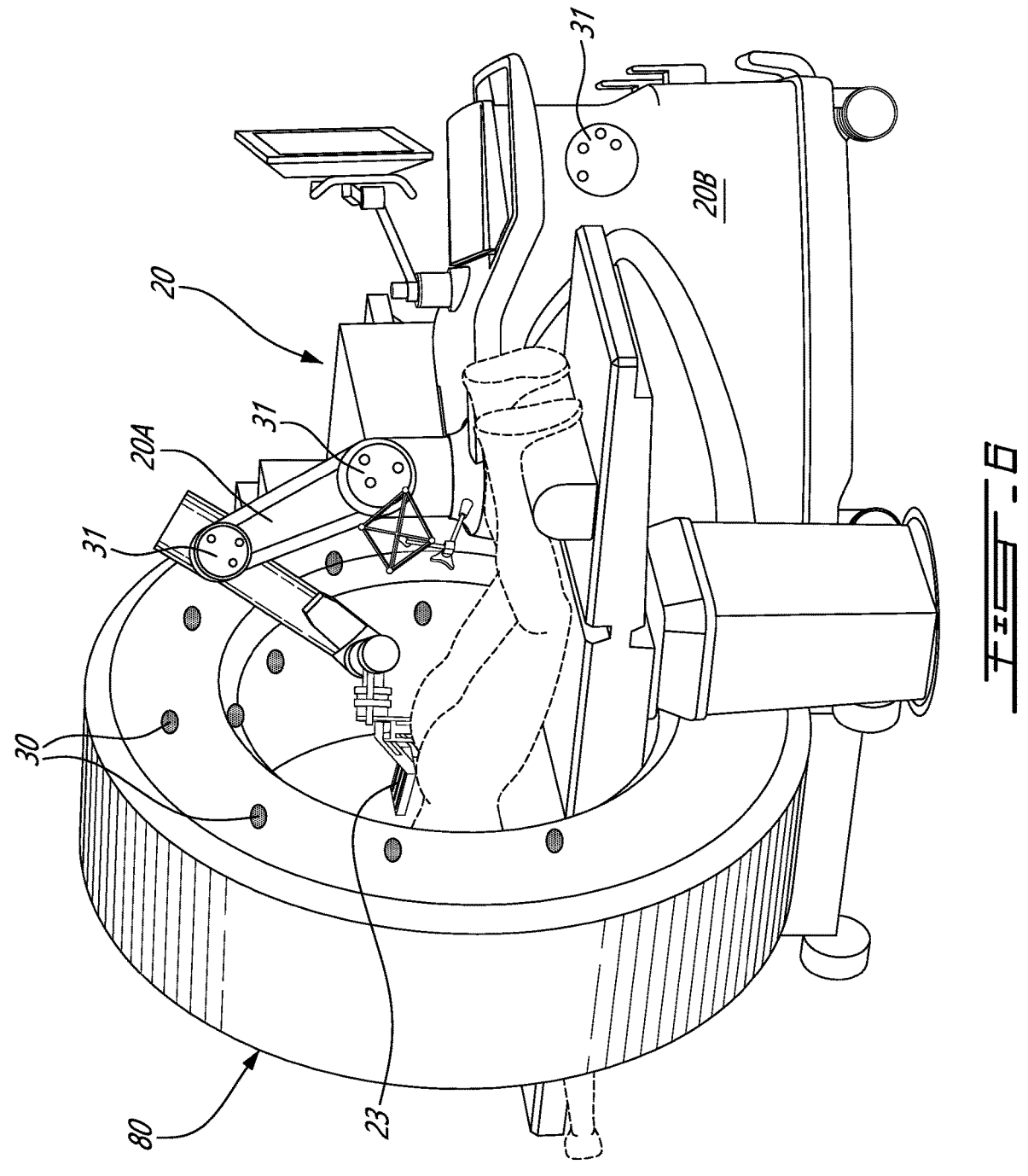
FIG. 6 is a perspective view of a robot of the robotic surgery system relative to imaging equipment, in accordance with a variant of the present disclosure.

Referring to FIG. 6, the robotic surgery system 10 is shown with imaging equipment 80. In FIG. 6, the imaging equipment 80 is shown as being an O-arm. The imaging equipment 80 may be any appropriate type of imaging equipment, including C-arm. In a variant, the imaging equipment is radiographic equipment that produces Xray images. The imaging technique may also be fluoroscopy for example.

When such imaging equipment 80 is used, it may be necessary to synchronize or correlate the images with the position and orientation of the patient, tools, and robot arm 20A/end effector 23, at time positions, i.e., what was the position and orientation of the various objects at the moment of imaging. Accordingly, the imaging equipment 80 may be provided with trackers 30 to establish such a time position correlation. Moreover, the approach described above, in which the robot 20 is part of a CMM has its fixed portion tracked (e.g., via tracking through the surgical drape), allows the robotic surgery system 10 to locate the robot 20 in the frame of reference. Stated differently, the frame of reference can adjust the position and orientation of the various equipment relative to the robot 20, so as to minimize disruptions in the tracking, and alleviate the need for a complete recalibration. This is described below for FIGS. 7 and 9.

Now that the various components of the robotic surgery system 10 have been described, a contemplated procedure performed with the robotic surgery system 10 or with a similar CAS system is set forth, with reference to FIGS. 1 and 2.

A flow chart illustrative of a method for tracking an end effector of a robot in computer-assisted surgery is shown at 700 in FIG. 7, and is an example of a procedure that may be performed by the CAS controller 50 and/or other parts of the robotic surgery system 10 of the present disclosure. For example, the method 700, and methods 800 and 900 described below, may be computer-readable program instructions in the non-transitory computer-readable memory 52 for example, and executable by the processing unit 51 communicatively coupled to the processing unit 51.

According to step 702, a referential tracking data for a first part of a robot is obtained using optical tracking relative to a frame of reference. In the robotic surgery system 10, the first part of the robot 20 may be the base 20B, using the trackers 30 on the structure 31. Though it may move, the base 20B is typically fixed during surgery, such that it may serve as a reference, as part of the CMM. The optical tracking may be the tracker device 40, also part of the CMM. The frame of reference is fixed in space, and the tracked first part of the robot 20 and the tracker device 40 may refer to the fixed frame of reference to locate themselves. In a variant, the trackers 30 are in a non-recorded arrangement on the robot 20. Step 702 may include observing the robot 20 and its trackers 30, and record the geometry of the trackers 30 on the robot 20. Stated differently, an optical tracker profile may be created for the robot 20, as part of step 702, or in a preceding step. The optical tracker profile created for the robot 20 may be the CMM for a remainder of the procedure. Step 702 may be repeated in another surgical procedure(s) or the CMM may be reused in other surgical procedure(s).

According to step 704, tool tracking data (e.g., encoder data in the joints of the robot arm 20A) may be concurrently obtained for an end effector of the robot arm 20A in the frame of reference. In an embodiment, this is done using the sensors 25 in the robot arm 20A. Step 704 may also include tracking an object, such as another robot arm 20A, a tool used in free hand movement, and a patient, such as a bone B of the patient. The robot coordinate tracking data of step 704 may be redundant over the optical tracking date of step 702. Such tracking may also include the use of dedicated trackers 30.

According to step 706, the position and orientation of the end effector in the frame of reference is continuously tracked and output, using the tool tracking data, i.e., the robot coordinate tracking data. The CAS controller 50 may continuously output tracking data indicating the position and orientation of the end effector 23 in the frame of reference, for example relative to the object, also concurrently tracked in the frame of reference.

According to step 708, the position and orientation of the end effector in the frame of reference may be continuously adjusted when the referential tracking data indicates a movement of the robot 20 and/of the optical tracking, in the frame of reference. More specifically, as the base 20B or like fixed part of the robot 20 is tracked by the optical tracking performed by the tracker device 40, it is possible to detect a relative movement between same. Stated differently, the tracker device 40 may recalibrate itself relative to the robot 20 once relative movement is detected, using the CMM defined by the trackers 30 of the robot 20 (such as those on the base 20B), to resume optical tracking.

For the methods described herein, when the plurality of trackers 30 are rigidly attached at various locations on the robot 20, such as on the robot arm 20A and on the base 20B, an initialization step may be done to register tracking data with the tracker device 40, and to compute position data for each tracker 30 in a kinematic model of the robot arm 20A. This may be known as creating a CMM file for the robot 20, or registering the robot 20 as CMM for a remainder of the surgical procedure. After this step, it is possible to compute the position of each tracker 30 according to the current articular position of the robot arm 20A, and sensors 25 can contribute. This is possible when the robot arm 20A is static but also in real time during robot moves. Comparing computed positions of each tracker 30 to the positions returned by the tracker device 40 may allow a detection of a loss of optical tracking accuracy coming from the robot arm 20A. This verification works even if some trackers 30 are hidden, due to the redundancy of trackers 30 in quantity.

Because of the redundancy of tracking, notably by the data from the sensors 25 and the data from the optical tracking, the system 10 may adjust to movement between components of the CMM, as the movement can be quantified. Accordingly, the surgical workflow may not need to pause for a complete recalibration of the robot 20 and of the patient to be done in the frame of reference. The system 10 may quantify the adjustment resulting from the relative movement of the robot 20 and/or the tracker device 40, and the surgical workflow may be continued.

The distinct sources of tracking data, i.e., the embedded tracking from the sensors 25 in the robot arm 20, and optical tracking using the robot base 20A as CMM, such as through the surgical drape for any of the optical tracking steps of method 700 (or methods 800 and/or 900), and other trackers 30, may be used to ensure that sufficient tracking data is available for the tracking module 60 (FIG. 2) to determine a position of the bone B and of the end effector 23 in the frame of reference continuously. The tracking module 60 may adjust the readings if movement is detected for the tracker device 40, with the configuration of the robotic surgery system 10.

The robotic surgery system 10 may perform continuous tracking. This means that the tracking may be performed continuously during discrete time periods of a surgical procedure. Continuous tracking may entail pauses, for example when the bone is not being altered. However, when tracking is required, the robotic surgery system 10 may perform a continuous tracking output, with any disruption in the tracking output triggering an alarm or message to an operator. The methods described herein may limit or reduce disruptions in the tracking, notably due to movements of the robot 20 and/or tracker device 40. If movements are detected, the time required to recalibrate the robotic surgery system 10.

Referring to FIG. 8, a flow chart illustrative of a method for operating a robotic surgery system in computer-assisted surgery is shown at 800, and is an example of a procedure that may be performed by the CAS controller 50 and/or other parts of the robotic surgery system 10 of the present disclosure.

According to step 802, tool tracking data is obtained for a robot using optical tracking of optically-detected trackers on a robot. In the robotic surgery system 10, the end effector 23 and/or other parts of the robot arm 20 is(are) tracked using the tracker device 40, and the trackers 30. Step 802 may also include tracking an object, such as another robot arm 20A, a tool used in free hand movement, and a patient, such as a bone B of the patient. Such tracking may also include the use of dedicated trackers 30.

According to step 804, the position and orientation of the end effector 23 is continuously tracked and output in a frame of reference, using the tool tracking data. The CAS controller 50 may continuously output tracking data indicating the position and orientation of the end effector 23 in the frame of reference, for example relative to the object, also concurrently tracked in the frame of reference.

According to step 806, a signalling interaction from an operator may be identified, the signalling interaction being to interact with an operating system of the robotic surgery system. This signalling interaction may be by visually detecting a temporary disappearance of a first predetermined tracker (a.k.a., predetermined marker) from the optically-detected trackers on the robot, irrespective of a position of an end effector of the robot. For example, tracker 30A may be assigned a given command, such as "enter". A user may block the line of sight between the tracker 30A and the tracker device 40, such that the tracker 30A is not visible, not seen by the tracker device 40. Stated differently, it disappears. This may be for a fixed amount of time, e.g., 1 second, or may require a particular disappearance, such as a sequence of two disappearances, equivalent to a double click. In an embodiment, such signalling interaction may only occur in given moments of the surgical workflow, when user commands are required. The predetermined tracker 30A may be separated from the tracker device 40 by a surgical drape, the tracker device 40 obtaining the tool tracking data of the robot 20 and identifying the signalling interaction by using the optical tracking through the surgical drape.

In an embodiment, the signalling interaction is irrespective of a position of the end effector 23. This signalling interaction may be said to be unrelated to tracking data, in that it is independent of the tracking action of the end effector 23.

Step 806 may include identifying a signalling interaction from the operator to interact with the operating system of the robotic surgery system by visually detecting a temporary disappearance of a second predetermined tracker from the optically-detected trackers on the robot. For example, the second predetermined tracker may be for a second type of command.

According to step 808, a command entry in the operating system is caused in response to the signalling interaction identified. For example, an enter command is effected. Other types of commands may be associated with the tracker 30A. Moreover, tracker 30B may be associated with a second command, differing from the first command. For example, the tracker 30B may be associated with a "back" command. In step 808, there is caused another command entry in the operating system in response to the signalling interaction identified from the second predetermined tracker, e.g., tracker 30B.

Method 800, and more particularly detection of signalling interaction may only be activated during specific steps in the surgical workflow in order to avoid activations due to surgery gestures during which the operator may hide the trackers 30. Additional options are envisaged to prevent false positive detection: Activate only those interactions when a vigilance device is pressed; Ask the operator to perform specific maneuvers, such as hiding quickly two times in a row the tracker 30, similarly to the double click for a computer mouse.

To summarize, using the trackers 30 directly on the robot arm 20A can allow the operator to interact with the arm 20A by hiding and showing some trackers 30 in order to execute actions on the applicative software. The tracker device 40 returns in real time the visibility status of each tracker 30 fixed on the arm 20A. Therefore, as soon as one of them is hidden, the information is transmitted to the operating system that is able to perform action accordingly. To do so it may be necessary to identify the trackers 30 so the operator knows which one needs to be used for signalling interactions. In a variant, trackers 30 are identified with colours: each tracker 30 may be surrounded by a simple colour so the operator associates trackers 30 to actions. In a variant, a red tracker 30 can be associated to a "cancel" button whereas a green tracker 30 could be the "OK" button.

Referring to FIG. 9, a flow chart illustrative of a method for tracking an end effector of a robot in computer-assisted surgery is shown at 900, and is another example of a procedure that may be performed by the CAS controller 50 and/or other parts of the robotic surgery system 10 of the present disclosure.

According to step 902, a referential tracking data for a first part of a robot is obtained using optical tracking relative to a frame of reference. In the robotic surgery system 10, the first part of the robot 20 may be the base 20B, using the trackers 30 on the structure 31. Though it may move, the base 20B is typically fixed during surgery, such that it may serve as a reference, as part of the CMM. The optical tracking may be the tracker device 40, also part of the CMM. The frame of reference is fixed in space, and the tracked first part of the robot 20 and the tracker device 40 may refer to the fixed frame of reference to locate themselves. In a variant, the trackers 30 are in a non-recorded arrangement on the robot 20. Step 902 may include observing the robot 20 and its trackers 30, and record the geometry of the trackers 30 on the robot 20. Stated differently, an optical tracker profile may be created for the robot 20, as part of step 902, or in a preceding step. The optical tracker profile created for the robot 20 may be the CMM for a remainder of the procedure. Step 902 may be repeated in another surgical procedure(s) or the CMM may be reused in other surgical procedure(s).

According to step 904, tool tracking data may be concurrently obtained for an end effector of the robot arm in the frame of reference. In an embodiment, this is done using the sensors 25 in the robot arm 20A. Step 904 may also include tracking an object, such as another robot arm 20A, a tool used in free hand movement, and a patient, such as a bone B of the patient. The robot coordinate tracking data of step 904 may be redundant over the optical tracking data of step 902. Such tracking may also include the use of dedicated trackers 30.

According to step 906, imaging equipment tracking data may be concurrently obtained for an imaging equipment in the frame of reference. For example, the imaging equipment is that shown at 80 in FIG. 6.

According to step 908, the position and orientation of the end effector in the frame of reference is continuously tracked and output, using the tool tracking data. The CAS controller 50 may continuously output tracking data indicating the position and orientation of the end effector 23 in the frame of reference, for example relative to the object, also concurrently tracked in the frame of reference.

According to step 910, the position and orientation of the equipment relative to the frame of reference may be continuously adjusted when the referential tracking data indicates a movement of the optical tracking, in the frame of reference. More specifically, as the base 20B or like fixed part of the robot 20 is tracked by the optical tracking performed by the tracker device 40, it is possible to detect a relative movement between same. The movement may for instance be due to the displacement of the robot 20 into the imaging equipment 80, such as shown in FIG. 6.

According to step 912, the position and orientation of the imaging equipment in the frame of reference may be output at a given time position, with a position and orientation of the end effector and of the object at the time position, the time position associated with an imaging step. For example, the tracker device 40 captures the position and orientation of the robot 20, of the patient, and of the imaging equipment 80, at a given time position, so as to correlate the various positions and orientations to the image(s) or footage associated with the imaging step.

Because of the redundancy of tracking, notably by the data from the sensors 25 and the data from the optical tracking, the system 10 may adjust to movement between components of the CMM, as the movement can be quantified. Accordingly, the surgical workflow may not need to pause for a complete recalibration of the robot 20 and of the patient to be done in the frame of reference. The system 10 may quantify the adjustment resulting from the relative movement of the robot 20 and/or the tracker device 40, and the surgical workflow may be continued. When the robot 20 is placed relative to the imaging equipment 80, the tracking module 60 may adjust the position and orientation of the imaging equipment 80 in the frame of reference.

Again, the distinct sources of tracking data, i.e., the embedded tracking from the sensors 25 in the robot arm 20, and optical tracking using the robot base 20A as CMM, such as through the surgical drape, and other trackers 30, ensure that sufficient tracking data is available for the tracking module 60 (FIG. 2) to determine a position of the bone B and of the end effector 23 in the frame of reference. The tracking module 60 may adjust the readings if movement is detected for the tracker device 40, with the configuration of the robotic surgery system 10.

The methods 700, 800, 900 described herein may control the robot arm 20A as a function of a position and orientation of the patient. Due to the quality of the tracking and the redundancy of trackers 30, it may be possible to perform various navigation functions with efficiency. For example, the tracking may ensure that any part of the robot arm 20A stays away from the surgical zone A. This functionality may be enhanced by the trackers 30 located on numerous links of the robot arm 20A, and tracking through the surgical drape D.

In a variant, the present disclosure pertains to a system for tracking an end effector of a robot in computer-assisted surgery, that may have a processing unit; and a non-transitory computer-readable memory communicatively coupled to the processing unit and comprising computer-readable program instructions executable by the processing unit for: obtaining referential tracking data for a first part of a robot using optical tracking relative to a frame of reference, and concurrently obtaining tool tracking data for an end effector of the robot arm in the frame of reference; and continuously tracking and outputting the position and orientation of the end effector in the frame of reference, using the tool tracking data, and concurrently adjusting the position and orientation of the end effector in the frame of reference when the referential tracking data indicates a movement of the first part of the robot and/of the optical tracking, in the frame of reference.

In a variant, the present disclosure pertains to a system for operating a robotic surgery system, that may have a processing unit; and a non-transitory computer-readable memory communicatively coupled to the processing unit and comprising computer-readable program instructions executable by the processing unit for: obtaining tool tracking data for a robot using optical tracking of optically-detected trackers on a robot; continuously tracking and outputting the position and orientation of the end effector in a frame of reference, using the tool tracking data; and identifying, from the optical tracking, a signalling interaction from an operator to interact with an operating system of the robotic surgery system by visually detecting a temporary disappearance of a first predetermined tracker from the optically-detected trackers on the robot, irrespective of a position of an end effector of the robot; and causing a command entry in the operating system in response to the signalling interaction identified.

The invention claimed is:

1. A system for operating a robotic surgery system, comprising:
   a processing unit; and
   a non-transitory computer-readable memory communicatively coupled to the processing unit and comprising computer-readable program instructions executable by the processing unit for:
      obtaining tool tracking data for a robot using optical tracking of optically-detected trackers on the robot;
      continuously tracking and outputting a position and orientation of an end effector in a frame of reference, using the tool tracking data; and
      identifying, from the optical tracking, a signalling interaction from an operator to interact with an operating system of the robotic surgery system by visually detecting a temporary disappearance of a first predetermined tracker from the optically-detected trackers on the robot, irrespective of a position of an end effector of the robot; and
      causing a command entry in the operating system in response to the signalling interaction identified.

2. The system according to claim 1, wherein the computer-readable program instructions are executable by the processing unit for obtaining object tracking data for an object.

3. The system according to claim 2, wherein the computer-readable program instructions are executable by the processing unit for continuously tracking and outputting a position and orientation of the object in the frame of reference, using the object tracking data, concurrently with tracking the tool in the frame of reference.

4. The system according to claim 3, wherein the computer-readable program instructions are executable by the processing unit for controlling the robot as a function of the position and orientation of the object.

5. The system according to claim 1, wherein the first predetermined tracker is separated from the optical tracking by a surgical drape, the system obtaining the tool tracking data of the robot and identifying the signalling interaction by using the optical tracking through the surgical drape.

6. The system according to claim 1, wherein the computer-readable program instructions are executable by the processing unit for identifying, from the optical tracking, a signalling interaction from the operator to interact with the operating system of the robotic surgery system by visually detecting a temporary disappearance of a second predetermined tracker from the optically-detected trackers on the robot.

7. The system according to claim 1, wherein the computer-readable program instructions are executable by the processing unit for causing another command entry in the operating system in response to the signalling interaction identified from a second predetermined tracker, the command entry associated with the second predetermined tracker differing from the command entry associated with the first predetermined tracker.

* * * * *